United States Patent [19]
Harrison et al.

[11] 4,172,941
[45] Oct. 30, 1979

[54] 7-[2-[ω-(1,3-DITHIOLAN-2-IMINO)SUB-STITUTED]-ACETYLAMINO]CEPHALOSPORANIC ACID DERIVATIVES

[75] Inventors: Boyd L. Harrison; Joseph E. Dolfini, both of Cincinnati, Ohio

[73] Assignee: Richardson-Merrell Inc., Wilton, Conn.

[21] Appl. No.: 905,215

[22] Filed: May 12, 1978

[51] Int. Cl.² .......................................... C07D 501/36
[52] U.S. Cl. ........................................ 544/28; 544/27; 424/246
[58] Field of Search ................................. 544/28, 27

[56] References Cited

U.S. PATENT DOCUMENTS

| | | | |
|---|---|---|---|
| 4,007,176 | 2/1971 | Berger et al. | 544/28 |
| 4,034,090 | 7/1977 | Berger et al. | 424/246 |
| 4,071,531 | 1/1978 | Berger et al. | 544/28 |

*Primary Examiner*—Nicholas S. Rizzo
*Attorney, Agent, or Firm*—William J. Stein; Eugene O. Retter; George W. Rauchfuss, Jr.

[57] ABSTRACT

Novel 7-[2-[ω-(1,3-dithiolan-2-imino)substituted]-acetylamino]cephalosporanic acid derivatives are described having useful antibacterial activity.

8 Claims, No Drawings

7-[2-[ω-(1,3-DITHIOLAN-2-IMINO)SUBSTITUTED]-ACETYLAMINO]CEPHALOSPORANIC ACID DERIVATIVES

FIELD OF THE INVENTION

This invention relates to certain cephalosporin derivatives useful as antibacterial agents and their method of preparation.

BACKGROUND OF THE INVENTION

Cephalosporin-type compounds belong to a well-known family of antibiotics that have been widely used in recent years for the treatment of various infectious diseases. A number of useful cephalosporins have been obtained by varying the substitution at the 3-position of the cephalosporin nucleus and by modifying the side-chain at the 7-position of the cephalosporin nucleus. The search continues, however, for new compounds having a high order of activity.

In an effort to improve and expand upon the properties of existing compounds, efforts have been directed towards the insertion of new moieties into the side chain of the cephalosporin molecule, located at the 7-position of the cephalosporin nucleus. We have discovered that the preparation of cephalosporin derivatives having a 1,3-dithiolan-2-imino group at the terminal end of the side chain produces compounds that are extremely useful antibacterial agents. More particularly, the preparation of cephalosporanic acid derivatives having an ω-(1,3-dithiolan-2-imino) moiety substituted at the terminal end of the side chain provides novel cephalosporin derivatives active against one or more gram-positive and gram-negative microorganisms. The compounds of this invention are therapeutically effective in the treatment of infectious diseases due to such gram-positive and gram-negative bacteria in poultry and in mammals including man. These compounds are also useful in topical germicidal preparations or as surface disinfectants.

SUMMARY OF THE INVENTION

The present invention relates to certain 7-(substituted)acetylamino cephalosporanic acid derivatives. More particularly, this invention relates to 7-[2-[ω-(1,3-dithiolan-2-imino)substituted]acetylamino]cephalosporanic acid derivatives useful as antibacterial agents, represented by the following structural formula

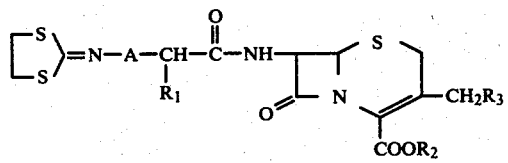

(I)

wherein A is selected from the group consisting of a sigma bond, phenylene and phenylenethio; $R_1$ is selected from the group consisting of hydrogen, phenyl, amino, hydroxy, carboxy and sulfo; $R_2$ is selected from the group consisting of hydrogen, formyloxymethyl and alkanoyloxymethyl in which the alkanoyl group contains from 2 to 5 carbon atoms; $R_3$ is selected from the group consisting of hydrogen, hydroxy, acetoxy, 5-methyl-1,3,4-thiadiazol-2-ylthio, 1-methyl-1,2,3,4-tetrazol-5-ylthio and 1,2,3-triazol-4-ylthio; and the pharmaceutically acceptable acid addition salts thereof.

Additionally, the present invention relates to the preparation of these 7-(substituted)acetylamino cephalosporanic acid derivatives and to their usefulness as antibacterial agents.

DETAILED DESCRIPTION OF THE INVENTION

As can be seen in formula (I) above, all of the compounds of the present invention contain a 1,3-dithiolan-2-imino moiety at the terminal position of the acetylamino side-chain in the 7-position of the cephalosporin nucleus. Thus, where the symbol A is a sigma bond, the 1,3-dithiolan-2-imino group is directly substituted on the acetic acid side chain and represents a sub-generic group of the invention.

Where the symbol A is a phenylene group, a second sub-generic group of compounds is designated in which the 1,3-dithiolan-2-imino moiety is substituted on the terminal extremity of the side chain or the para-position of the phenyl ring. For purposes of uniformity of nomenclature these compounds are designated as 2-[p-(1,3-dithiolan-2-imino)phenyl]acetylamino derivatives of cephalosporanic acid.

Where the symbol A is a phenylenethio group, the 1,3-dithiolan-2-imino moiety is again substituted in the para-position of the phenyl ring to form a third sub-generic group of compounds. To be consistent with the nomenclature employed, such compounds are designated as 2-[p-(1,3-dithiolan-2-imino)phenylthio]acetylamino derivatives of cephalosporanic acid.

The term cephalosporanic acid derivatives relates generically to the various specific cephalosporanic acids encompassed by the various substituents on the 3-methyl group of the cephalosporin nucleus as indicated by the symbol $R_3$. Thus, where $R_3$ is hydrogen the compounds are designated as desacetoxycephalosporanic acids. When $R_3$ is hydroxy the compounds are designated as belonging to a class of desacetylcephalosporanic acids. Where the symbol $R_3$ represents the acetoxy group, the compounds are specifically designated as cephalosporanic acids. Lastly, the symbol $R_3$ can represent a heterocyclic thioether attached to the 3-methyl group of the cephalosporin nucleus. The preferred heterocyclic thioethers include the 5-methyl-1,3,4-thiadiazol-2-ylthio group, the 1-methyl-1,2,3,4-tetrazol-5-ylthio group and the 1,2,3-triazol-4-ylthio group. To be consistent with the nomenclature employed herein these heterocyclic thioethers are designated as 3-[(substituted)thiomethyl]decephalosporanic acids.

The 2-position of the cephalosporanic nucleus is substituted with either a carboxylic acid or a carboxylic acid ester as indicated by the formyloxymethyl and alkanoyloxymethyl groups. The term alkanoyl as used in this regard includes those groups having a total of from 2 through 5 carbon atoms, as for example, acetyloxy, propionyloxy, butyryloxy, isobutyryloxy, 2-methylbutyryloxy, 3-methylbutyryloxy and 2,2-dimethylpropionyloxymethyl. These esters confer improved absorption properties upon the molecule and at the same time are physiologically labile. Thus, these esters are readily absorbed from the gastro-intestinal tract and are then enzymatically hydrolyzed to the corresponding cephalosporanic acids, thereby promoting oral activity.

The pharmaceutically acceptable salts of the compounds of formula (I) include the non-toxic, carboxylic acid salts that are formed with any suitable inorganic or organic base. Illustratively, these salts include those of alkali metals, as for example, sodium and potassium; alkaline earth metals, such as barium, calcium and magnesium; light metals of Group III A including aluminum; and organic primary, secondary and tertiary amines such as triethylamine, procaine, dibenzylamine, vinylamine, N,N'-dibenzylethylenediamine, dihydrobietylamine, N-(lower)alkylpiperidine and other amines that have been used to form non-toxic salts of antibiotics, such as with benzylpenicillin. These salts can be prepared via conventional means, as for example, contacting and neutralizing a solution of the free carboxylic acid in a polar solvent with a stoichiometric quantity of base and isolating the salt therefrom.

Also included within the term of pharmaceutically acceptable salts are the non-toxic organic or inorganic acid addition salts of the base compounds of formula (I), i.e., where $R_1$ is amino. Illustrative inorganic acids that form suitable acid addition salts include hydrochloric, hydrobromic, sulfuric and phosphoric acids in addition to acid metal salts such as sodium monohydrogen orthophosphate and potassium hydrogen sulfate. Illustrative organic acids which form suitable salts include mono, di- and tricarboxylic acids, as for example acetic, glycolic, lactic, pyruvic, malonic, succinic, glutaric, fumaric, malic, tartaric, citric, ascorbic, maleic, hydroxymaleic, benzoic, p-hydroxybenzoic, phenylacetic, cinnamic, salicyclic, 2-phenoxybenzoic and sulfonic acids such as methane sulfonic acid and 2-hydroxyethane sulfonic acid. The various pharmaceutically acceptable base or acid addition salts can exist in either a hydrated or a substantially anhydrous form.

In addition to the non-toxic carboxylic acid salts and the non-toxic acid addition salts of the base compounds, the term pharmaceutically acceptable salts includes the internal salts or zwitterions of the compounds of formula (I) when $R_1$ is amino. Such zwitterions are pharmaceutically equivalent to either the non-toxic carboxylic acid salts or the organic and inorganic acid addition salts mentioned above, and they also fall within the purview of the present invention.

Where $R_1$ is other than hydrogen, stereoisomerism occurs around the asymmetric carbon atom to which it is attached. The preferred and most active compounds are those having a D-configuration at the α-carbon atom in the 7-position side chain and are prepared from the corresponding D(—)-ω-(1,3-dithiolan-2-imino)substituted acetic acids.

Illustrative specific base compounds encompassed by formula (I) above include:

7-[2-(1,3-dithiolan-2-imino)acetylamino]cephalosporanic acid,

7-[2-amino-2-(1,3-dithiolan-2-imino)acetylamino]-desacetoxycephalosporanic acid, 7-[2-amino-2-(1,3-dithiolan-2-imino)acetylamino]-desacetylcephalosporanic acid, formyloxymethyl 7-[2-amino-2-(1,3-dithiolan-2-imino)-acetylamino]-3-[(5-methyl-1,3,4-thiadiazol-2-ylthio)methyl]-decephalosporanate, 7-[2-carboxy-2-(1,3-dithiolan-2-imino)acetylamino]-3-[(1-methyl-1,2,3,4-tetrazol-5-ylthio)methyl]decephalosporanic acid, 7-[2-carboxy-2-(1,3-dithiolan-2-imino)acetylamino]-3-[(1,2,3-triazol-4-ylthio)methyl]decephalosporanic acid, pivaloyloxymethyl 7-[2-carboxy-2-(1,3-dithiolan-2-imino)acetylamino]cephalosporanic acid, 7-[2-(1,3-dithiolan-2-imino)-2-hydroxyacetylamino]-desacetoxycephalosporanic acid, 7-[2-(1,3-dithiolan-2-imino)-2-hydroxyacetylamino]-desacetylcephalosporanic acid, acetyloxymethyl 7-[2-(1,3-dithiolan-2-imino)-2-hydroxyacetylamino]-3-[(5-methyl-1,3,4-thiadiazol-2-ylthio)-methyl]decephalosporanate, 7-[2-(1,3-dithiolan-2-imino)-2-phenylacetylamino]-3-[(1-methyl-1,2,3,4-tetrazol-5-ylthio)methyl]decephalosporanic acid, 7-[2-(1,3-dithiolan-2-imino)-2-phenylacetylamino]-3-[(1,2,3-triazol-4-ylthio)methyl]decephalosporanic acid, propionyloxymethyl 7-[2-(1,3-dithiolan-2-imino)-2-phenylacetylamino]-3-[(1,2,3-triazol-4-ylthio)methyl]-decephalosporanate, 7-[2-(1,3-dithiolan-2-imino)-2-sulfoacetylamino]-cephalosporanic acid, 7-[2-(1,3-dithiolan-2-imino)-2-sulfoacetylamino]-desacetoxycephalosporanic acid, butyryloxymethyl 7-[2-(1,3-dithiolan-2-imino)-2-sulfoacetylamino]desacetylcephalosporanic acid, 7-[2-[p-(1,3-dithiolan-2-imino)phenyl]acetylamino]-cephalosporanic acid, 7-[2-amino-2-[p-(1,3-dithiolan-2-imino)phenyl]acetylamino]desacetoxycephalosporanic acid, 7-[2-amino-2-[p-(1,3-dithiolan-2-imino)phenyl]acetylamino]desacetylcephalosporanic acid, formyloxymethyl 7-[2-amino-2-[p-(1,3-dithiolan-2-imino)-phenyl]acetylamino]-3-[(5-methyl-1,3,4-thiadiazol-2-ylthio)-methyl]decephalosporanate, 7-[2-carboxy-2-[p-(1,3-dithiolan-2-imino)phenyl]-acetylamino]-3-[(1-methyl-1,2,3,4-tetrazol-5-ylthio)methyl]-decephalosporanic acid, 7-[2-carboxy-2-[p-(1,3-dithiolan-2-imino)phenyl]-acetylamino]-3-[(1,2,3-triazol-4-ylthio)methyl]decephalosporanic acid, pivaloyloxymethyl 7-[2-carboxy-2-[p-(1,3-dithiolan-2-imino)phenyl]acetylamino]cephalosporanic acid, 7-[2-[p-(1,3-dithiolan-2-imino)phenyl]-2-hydroxyacetylamino]desacetoxycephalosporanic acid, 7-[2-[p-(1,3-dithiolan-2-imino)phenyl]-2-hydroxyacetylamino]desacetylcephalosporanic acid, acetyloxymethyl 7-[2-[p-(1,3-dithiolan-2-imino)-phenyl]-2-hydroxyacetylamino]-3-[(5-methyl-1,3,4-thiadiazol-2-ylthio)methyl]decephalosporanate, 7-[2-[p-(1,3-dithiolan-2-imino)phenyl]-2-phenylacetylamino]-3-[(1-methyl-1,2,3,4-tetrazol-5-ylthio)methyl]-decephalosporanic acid, 7-[2-[p-(1,3-dithiolan-2-imino)phenyl]-2-phenylacetylamino]-3-[(1,2,3-triazol-4-ylthio)methyl]-decephalosporanic acid, propionyloxymethyl 7-[2-[p-(1,3-dithiolan-2-imino)-phenyl]-2-phenylacetylamino]cephalosporanate, 7-[2-[p-(1,3-dithiolan-2-imino)phenyl]-2-sulfoacetylamino]desacetoxycephalosporanic acid, 7-[2-[p-(1,3-dithiolan-2-imino)phenyl]-2-sulfoacetylamino]desacetylcephalosporanic acid, butyryloxymethyl 7-[2-[p-(1,3-dithiolan-2-imino)-phenyl]-2-sulfoacetylamino]-3-[(5-methyl-1,3,4-thiadiazol-2-ylthio)-methyl]decephalosporanate, 7-[2-[p-(1,3-dithiolan-2-imino)phenylthio]acetylamino]-cephalosporanic acid, 7-[2-amino-2-[p-(1,3-dithiolan-2-imino)phenylthio]-acetylamino]desacetoxycephalosporanic acid, 7-[2-amino-2-[p-(1,3-dithiolan-2-imino)phenylthio]-acetylamino]desacetylcephalosporanic acid, formyloxymethyl 7-[2-amino-2-[p-(1,3-dithiolan-2-imino)-phenylthio]acetylamino]-3-[(5-methyl-1,3,4-thiadiazol-2-ylthio)methyl]decephalosporanate, 7-[2-carboxy-2-[p-(1,3-dithiolan-2-imino)phenylthio]-acetylamino]-3-[(1-methyl-1,2,3,4-tetrazol-5-ylthio)methyl]-decephalosporanic acid, 7-[2-carboxy-2-[p-(1,3-dithiolan-2-imino)phenylthio]-acetylamino]-3-[(1,2,3-triazol-4-ylthio)methyl]decephalosporanic acid, pivaloyloxymethyl 7-[2-carboxy-2-[p-(1,3-dithiolan-2-imino)phenylthio]acetylamino]cephalosporanic acid, 7-[2-[p-(1,3-dithiolan-2-imino)phenylthio]-2-hydroxyacetylamino]desacetoxycephalosporanic acid, 7-[2-[p-(1,3-dithiolan-2-imino)phenylthio]-2-hydroxyacetylamino]desacetylcephalosporanic acid, acetloxymethyl 7-[2-[p-(1,3-dithiolan-2-imino)-phenylthioo]-2-hydroxyacetylamino]-3-[(5-methyl-1,3,4-thiadiazol-2-ylthio)methyl]decephalosporanate, 7-[2-[p-(1,3-dithiolan-2-imino)phenylthio]-2-phenylacetylamino]-3-[(1-methyl-1,2,3,4-tetrazol-5-ylthio)methyl]-decephalosporanic acid, 7-[2-[p-(1,3-dithiolan-2-imino)phenylthio]-2-phenylacetylamino]-3-[(1,2,3-triazol-4-ylthio)methyl]-decephalosporanic acid, propionyloxymethyl 7-[2-[p-(1,3-dithiolan-2-imino)-phenylthio]-2-phenylacetylamino]cephalosporanate, 7-[2-[p-(1,3-dithiolan-2-imino)phenylthio]-2-sulfoacetylamino]desacetoxycephalosporanic acid, 7-[2-[p-(1,3-dithiolan-2-imino)phenylthio]-2-sulfoacetylamino]desacetylcephalosporanic acid, and pivaloyloxymethyl 7-[2-[p-(1,3-dithiolan-2-imino)-phenylthio]-2-sulfoacetylamino]-3-[(5-methyl-1,3,4-thiadiazol-2-ylthio)methyl]decephalosporanate.

The products of the present invention are prepared by the condensation of an ω-(1,3-dithiolan-2-imino)substituted acetic acid of structure (II) with a 7-aminocephalosporanic acid, having the structure (III), as shown in the following reaction sequence wherein the symbols A, $R_1$, $R_2$ and $R_3$ are as previously defined.

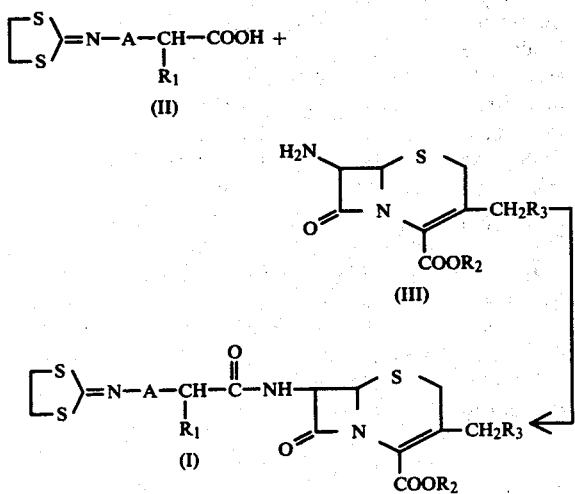

The ω-(1,3-dithiolan-2-imino)substituted acetic acids are prepared by the condensation in solution of an S-alkylated salt of 1,3-dithiolane-2-thione(IV) with an ω-amino substituted acetic acid (V), schematically illustrated as follows:

Wherein the symbol X is halogen and the remaining symbols have the same meaning as previously described. The S-alkylated salts of 1,3-dithiolane-2-thione are readily prepared by the alkylation of 1,3-dithiolane-2-thione, known commercially as ethylenetrithiocarbonate. The various ω-amino substituted acetic acids depicted by formula (V) above are either commercially available or are readily prepared by those versed in the art using methods described in the literature. Illustrative of these ω-amino substituted acetic acids are such commonly available acids as glycine, phenylglycine, p-aminophenylglycine, p-aminophenylacetic acid, p-aminophenylthioacetic acid, p-aminomandelic acid, 2-aminomalonic acid and p-aminophenylsulfoacetic acid.

In general the ω-(1,3-dithiolan-2-imino)substituted acetic acids (II) are prepared by dissolving or suspending the ω-amino substituted acetic acid, or a protected derivative thereof, in a suitable solvent to which the S-alkylated salt of 1,3-dithiolane-2-thione is added. Condensation occurs at a temperature of from 0° to 50° C. over a period of from 1 to 12 hours. Preferably, the condensation reaction is conducted at room temperature in an inert atmosphere, such as nitrogen or argon, with a reaction time of 30 minutes generally being all that is required for the reaction to go to completion.

Suitable solvents include diethyl ether, tetrahydrofuran, acetonitrile, methanol and aqueous solutions thereof with water, dimethylformamide and dioxane being the solvents of choice. Solution of the ω-amino substituted acetic acids (V) and their subsequent condensation with the S-alkylated salt of 1,3-dithiolan-2-thione is facilitated by the optional addition of a suitable base such as pyridine, sodium bicarbonate or an alkylamine. When the symbol $R_1$ represents the amino or hydroxyl radical, it may be further desirable to employ a suitable protecting group. Suitable protecting groups include the benzyloxycarbonyl, t-butoxycarbonyl, benzyl, p-methoxybenzyl, trichloroethoxycarbonyl, acetyl and dichloroacetyl derivatives of the α-amino or α-hydroxy substituents. Alternatively, when $R_1$ is amino, condensation of the various α,ω-diamino substituted acetic acids can be conducted at the isoelectric point of the diamino acid, thereby permitting condensation to take place at the more nucleophilic ω-amino nitrogen atom.

The various 7-aminocephalosporanic acids employed herein (III) are well-known compounds previously described in the literature. Thus, hydrolysis of cephalosporin C results in the formation of 7-aminocephalosporanic acid as described by Loder et al., Biochem. J. 79, 408–16 (1961) and represented by the formula

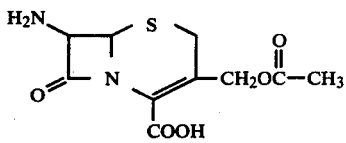

The compound 7-aminodesacetoxycephalosporanic acid, having the formula

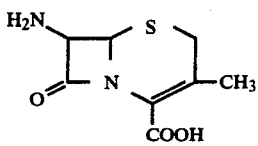

is prepared by the catalytic reduction of cephalosporin C, followed by the hydrolytic removal of the 5-aminoadipoyl side chain as described in U.S. Pat. No. 3,129,224.

Treatment of cephalosporin C with an acetyl esterase prepared from orange peel as described by Jeffery et al., Biochem J. 81, 591 (1961) results in the formation of 3-hydroxymethyl-7-aminodecephalosporanic acid or 7-aminodesacetylcephalosporanic acid having the formula

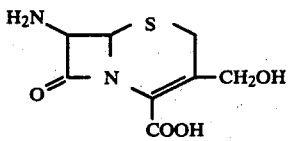

The ω-(1,3-dithiolan-2-imino)substituted acetic acids (II) are coupled through the carboxylic acid function of the acetic acid to the free 7-amino group of the cephalosporanic acid (III), either with or without the presence of a suitable base. Suitable bases that can be employed for the coupling reaction include pyridine, sodium bicarbonate or trialkylamine. The ω-(1,3-dithiolan-2-imino)substituted acetic acids are generally coupled in the form of their activated acid derivatives or functional equivalents, as for example the corresponding acyl halides, acid anhydrides, mixed anhydrides, particularly those mixed anhydrides prepared from stronger acids. A frequently used activated acid derivative is a mixed anhydride synthesized from an ω-(1,3-dithiolan-2-imino)substituted acetic acid with ethyl chloroformate or isobutylchloroformate.

Condensation of the ω-(1,3-dithiolan-2-imino)substituted acetic acid may be facilitated by initially reacting the free acid with a suitable coupling agent. Suitable coupling agents useful in this reaction include N,N'-carbonyldiimidazole, N,N'-dicyclohexylcarbodiimide, N,N'-diisopropylcarbodiimide, N-cyclohexyl-N'-(2-morpholinoethyl)carbodiimide, metho-p-toluenesulfonate, 2-ethoxy-1-ethoxycarbonyl-1,2-dihydroquinoline (EEDQ) or 2-isobutoxy-1-isobutoxycarbonyl-1,2-dihydroquinoline.

The 7-aminocephalosporanic acids (III) can be coupled as the free acid. Preferably, however, they are condensed in the form of their salts or as easily hydrolyzed esters. Suitable salts include the sodium or trialkylammonium salts in which the alkyl group contains from 1 to 5 carbon atoms. Suitable esters include any of the esters disclosed in U.S. Pat. No. 3,284,451, or any of the silyl esters disclosed in U.S. Pat. No. 3,249,622.

Following the coupling reaction these esters are readily removed to yield the products of this invention.

In general, the coupling reaction is conducted in the presence of a suitable solvent such as acetone, dioxane, chloroform, ethylene chloride, dichloromethane and tetrahydrofuran. In certain instances, mixtures of water and a miscible organic solvent may be advantageously employed. The temperature of the coupling reaction varies from $-30°$ C. to $100°$ C. with the preferred temperature being at room temperature or slightly below. The reaction time can vary anywhere from 15 minutes to as long as 36 hours. Preferably, a period of from 1 to 8 hours is employed.

Where the symbol $R_1$ represents the amino or hydroxy group, these groups are generally protected during the coupling reaction with suitable blocking groups useful for this purpose. Thus, the amino blocking group can be a proton, as in the case of an amine hydrochloride salt, or can include such blocking agents as the benzyloxycarbonyl, trichloroethoxycarbonyl, trifluoroacetyl, p-methoxycarbobenzoxy, p-nitrocarbobenzoxy and t-butyloxycarbonyl groups with the t-butyloxycarbonyl group being the blocking agent of choice. Various hydroxyl blocking agents that can be employed include the dichloroacetyl, trifluoroacetyl, benzyl, benzhydryl, trityl, p-methoxybenzyl, tetrahydropyranyl, t-butyldimethylsilyl, trimethylsilyl and methoxymethyl groups with the trimethylsilyl group being the blocking group of choice.

After coupling the blocking groups are removed by processes well-known to the art to yield the desired 7-[2-[ω-(1,3-dithilan-2-imino)substituted]acetylamino]-cephalosporanic acid derivatives of the present invention. Thus for example, in the case of the t-butoxycarbonyl or p-methoxycarbobenzoxy protected amino group, the blocking agents are readily removed by treatment with trifluoroacetic acid, formic acid or hydrochloric acid gas dissolved in nitromethane. The benzyloxycarbonyl and p-nitrocarbobenzoxy groups can be removed via catalytic hydrogenation. The trichloroethoxycarbonyl group can be removed by treatment with zinc in acetic acid. With respect to the hydroxyl protecting dichloroacetyl and trifluoroacetyl groups, they are readily removed by treatment with a dilute aqueous sodium bicarbonate solution. The benzyl, benzhydryl and trityl protecting hydroxyl groups can be removed via catalytic hydrogenation. The p-methoxybenzyl protecting group can be removed by simple acid treatment, whereas the trimethylsilyl protecting group is readily removed by treatment with water or dilute aqueous acid.

In certain cases, as where the symbol A represents a sigma bond and $R_1$ is hydrogen, an alternative procedure can be employed to synthesize the cephalosporins of the present invention. This procedure is schematically illustrated below wherein the symbol B represents one of the aforementioned amino protecting groups and the symbols $R_2$ and $R_3$ are as previously defined.

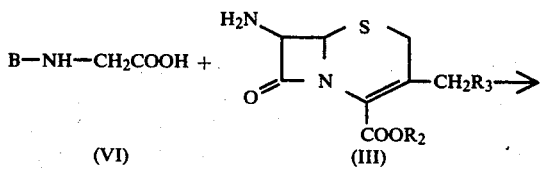

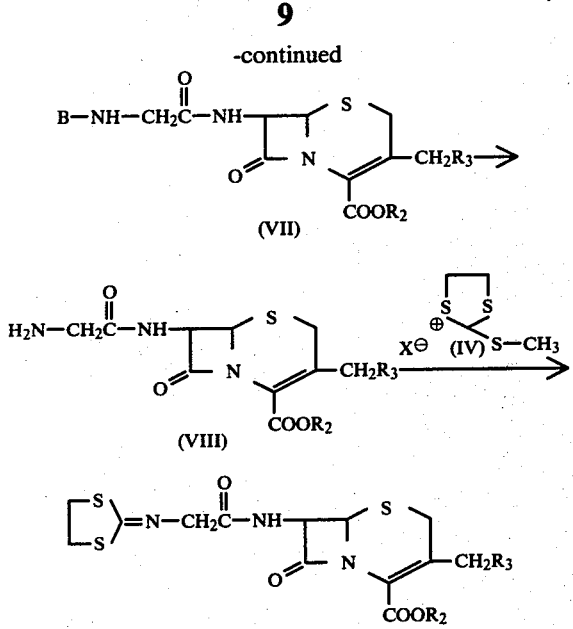

Thus, an N-protected glycine (VI) is coupled to a cephalosporanic acid (III) in a manner as previously described to form a cephalosporin intermediate (VII). The N-blocking group can be removed in accordance with the procedures previously described to form a 7-aminoacetylamino cephalosporanic acid (VIII). Condensation of this free cephalosporanic acid with the S-methyl salt of 1,3-dithiolane-2-thione (IV) in a manner analogous to that previously described for the preparation of the ω-(1,3-dithiolan-2-imino)substituted acetic acids (II) provides the cephalosporanic acids of formula (I) wherein the symbol A is a sigma bond and the symbol $R_1$ is hydrogen.

A preferred group of 7-[2-[ω-(1,3-dithiolan-2-imino)-substituted]acetylamino]cephalosporanic acids are those containing a methylthioheterocycle group at the 3-position of the cephalosporin nucleus. In addition to the condensation or acylation procedure described above, such compounds can be prepared by the displacement of the 3-acetoxy group of a 7-[2-[ω-(1,3-dithiolan-2-imino)substituted]-acetylamino]cephalosporanic acid derivative. This displacement or solvolysis of the acetoxy group of the cephalosporin nucleus is a well-known reaction as described in U.S. Pat. Nos. 3,516,997 and 3,641,021. The acetoxy group is displaced with a heterocyclic thiol such as 5-methyl-1,3,4-thiadiazol-2-thiol, 1-methyl-1,2,3,4-tetrazol-5-thiol or 1,2,3-triazol-4-thiol in an aqueous solvent such as water or buffered aqueous solutions at a temperature ranging from about 25° C. to 150° C. Preferably, a temperature range of from 50° C. to 100° C. and a pH of from about 4.0 to 9.0 is employed. Suitable aqueous solutions include those selected from the group consisting of water, or an aqueous solution of acetone, tetrahydrofuran and dimethylformamide. When the symbol $R_1$ represents either amino or hydroxy, the solvolysis can be conducted using either blocked or unblocked derivatives. Preferably, however, in such a case the solvolysis reaction utilizes one of the blocking groups earlier mentioned.

In certain instances the displacement of the acetoxy group from the methyl group at the 3-position results in the migration of the double bond to the $\Delta^3$-position of the cephalosporin nucleus. Under those circumstances the position of the double bond can be re-established by the oxidation of the ring sulfur to the sulfoxide with such oxidizing agents as hydrogen peroxide, sodium metaperiodate or an organic peracid. Subsequent reduction of the sulfoxide by means of catalytic hydrogenation or sodium dithionite provides the desired cephalosporin derivatives which are unsaturated in the $\Delta^2$-position of the cephalosporin nucleus.

The compounds contemplated within the scope of this invention include not only the various cephalosporanic acids previously described, but certain esters thereof as indicated by the symbol $R_2$. The preferred esters of this invention include the formyloxymethyl, acetyloxymethyl and the pivaloyloxymethyl esters. These esters are generally prepared by condensation of an ω-(1,3-dithiolan-2-imino)substituted acetic acid of formula (II) with the corresponding 7-aminocephalosporanic ester of formula (III). Such esters can be prepared in accordance with the procedures described by Binderup et al., Journal of Antibiotics, 24, 767 (1971).

The novel compounds of the present invention are orally and parenterally active having good antibacterial activity. Thus, they are useful antimicrobial agents having a broad spectrum of antimicrobial activity in vitro against standard laboratory microorganisms which are used to screen activity against pathogenic bacteria. The antibacterial spectrum of typical compounds of the present invention can be determined in a standard manner by the agar-dilution streakplate technique commonly employed for the testing of new antibiotics.

The high in vitro antibacterial activity of the novel compounds of this invention not only makes them useful as pharmacological agents per se, but makes them useful as additives for animal feeds, as well as additives for materials which are subject to microbial deterioration, such as cutting oils and fuel oils. These compounds are also useful for their antibacterial effect in soaps, shampoos and in topical compositions for the treatment of wounds and burns.

The invention described herein is more particularly illustrated in conjunction with the following specific examples.

EXAMPLE 1

S-Methyl 1,3-dithiolane-2-thione iodide 1,3-Dithiolane-2-thione, (ethylenetrithiocarbonate) 13.6 g, is dissolved in 25 ml of reagent nitromethane and treated at room temperature with 14.2 g of methyl iodide via dropwise addition with stirring under an atmosphere of nitrogen. The reaction mixture is wrapped with foil for light protection and stirring is continued overnight. The crystals that form are filtered, washed with dry benzene and dried in vacuo to yield 20.9 g of brown colored, crystalline S-methyl 1,3-dithiolane-2-thione iodide having a m.pt. of 80°–3° C.

EXAMPLE 2

α-(1,3-Dithiolan-2-imino)-α-phenylacetic acid

D-α-phenylglycine, 1.51 g, is suspended in 30 ml of a 1:1 dioxane-water solution and dissolved by the addition of 15 ml of triethylamine. The solution is cooled in an icesalt bath, treated with 3.06 g of S-methyl 1,3-dithiolane-2-thione iodide. The reaction mixture is stirred overnight, evaporated to approximately ½ volume in vacuo, filtered and extracted with diethyl ether. The aqueous layer is acidified to pH 2.0 with a solution of 1 N HCl and extracted with ethyl acetate. The organic extracts are combined, dried over anhydrous magnesium sulfate and evaporated to dryness in vacuo to yield 0.770 g of an off-white solid having a m.pt. of 67°-82° C. (dec.). An NMR spectrum indicates this material to be the desired Dα-(1,3-dithiolan-2-imino)-α-phenylacetic acid.

Following essentially the same procedure but substituting glycine for the D-α-phenylglycine above results in the formation of α-(1,3-dithiolan-2-imino)acetic acid.

EXAMPLE 3

4-(1,3-Dithiolan-2-imino)benzeneacetic acid

Triethylamine, 15 ml, and 1.51 g of p-aminophenylacetic acid are dissolved at room temperature in 15 ml of sieve-dried dimethylformamide under an inert atmosphere of argon. To this solution is added 3.06 g of S-methyl 1,3-dithiolane-2-thione iodide and the reaction mixture is stirred at room temperature for a period of four hours. The reaction mixture is poured into 100 ml of water, extracted four times with 50 ml portions of methylene chloride followed by two 100 ml extractions with diethyl ether. The aqueous solution is adjusted to pH 1.0 using a concentrated hydrochloric acid solution. The tan solid which precipitates is removed by filtration and dried in vacuo to yield 1.05 g of the desired crude product. The crude material is recrystallized from a hot ethanol-dimethylformamide mixture, filtered and washed with cold ethanol to yield 0.805 g of light tan colored 4-(1,3-dithiolan-2-imino)benzeneacetic acid having a m.pt. of 233°-5° C. (dec.).

Following essentially the same procedure but substituting α-sulfo-4-aminobenzeneacetic acid and α-carboxy-4-aminobenzeneacetic acid for the p-aminophenylacetic acid above, results in the preparation of 4-(1,3-dithiolan-2-imino)-α-sulfobenzeneacetic acid and 4-(1,3-dithiolan-2-imino)-α-carboxybenzeneacetic acid, respectively.

EXAMPLE 4

4-(1,3-Dithiolan-2-imino)benzenethioacetic acid

The compound p-aminobenzenethiacetic acid, 7.32 g, is dissolved in 75 ml of sieve-dried dimethylformamide that contains 75 ml of triethylamine. S-methyl 1,3-dithiolane-2-thione iodide, 12.2 g, is added in portions thereto. The reaction mixture is stirred for a period of two hours, and poured into an ice-water mixture. The resulting mixture is extracted several times with methylene chloride followed by an extraction with diethyl ether. The aqueous layer which remains is adjusted to a pH of 3.0 using concentrated hydrochloric acid, whereupon the oil which separates is extracted into ethyl acetate. The ethyl acetate extracts are combined, dried over anhydrous magnesium sulfate and the solvent removed in vacuo. The remaining residue is crystallized from a chloroform-ether solution, recrystallized from a 50:50 chloroform-ethanol solution, and recrystallized once again from a hot ethanol-water solution to yield 3.02 g of 4-(1,3-dithiolan-2-imino)benzenethiacetic acid having a m.pt. of 129°-133° C.

Following essentially the same procedure but substituting α-sulfo-p-aminobenzenethioacetic acid and α-carboxy-p-aminobenzenethioacetic acid for the p-aminobenzenethioacetic acid above results in the formation of 4-(1,3-dithiolan-2-imino)-α-sulfo-benzenethioacetic acid and 4-(1,3-dithiolan-2-imino-α-carboxy-benzenethioacetic acid, respectively.

EXAMPLE 5

7-[2-(1,3-Dithiolan-2-imino)acetylamino]cephalosporanic acid, sodium salt

N-t-butyloxycarbonylglycine, 6.13 g, is dissolved in 175 ml of tetrahydrofuran containing 3.54 g of triethylamine, cooled to −10° C. and 4.6 ml of isobutylchloroformate added thereto while maintaining the temperature at −10° C. This mixed anhydride solution is stirred and a cold solution of the 7-aminocephalosporanic acid triethylamine salt, dissolved in 100 ml of a 1:1 tetrahydrofuran-water solution, is added thereto while maintaining the temperature at −10° C. or below. The reaction mixture is stirred at this temperature for approximately one hour and then permitted to warm to room temperature with continued stirring for an additional 2 hours. The reaction mixture is poured into 60 ml of water and extracted with three 50 ml portions of ethyl acetate. The aqueous solution so obtained is adjusted to a pH of 3.0 with a 1 N hydrochloric acid solution, layered with ethyl acetate and extracted twice with additional ethyl acetate. The combined ethyl acetate extracts are dried (anhydrous MgSO4) and evaporated to dryness in vacuo to yield 8.7 g 7-[N-t-butyloxycarbonylglycylamino]cephalosporanic acid. The t-butyloxycarbonyl protecting group is removed by treating with 20 ml of cold trifluoroacetic acid, warmed to room temperature and stirred for 10 minutes. The mixture is poured into 300 ml of stirred diethyl ether to precipitate 6.8 g of an off-white trifluoroacetate salt of 7-glycylaminocephalosporanic acid.

The trifluoroacetate salt obtained in this manner is dissolved in 100 ml of water, filtered and 6 teaspoons of a water washed weakly basic polyphenol-formaldehyde anionic exchange resin (Mallinckrodt IR-4B) is added to the filtrate. The mixture is stirred approximately one hour, filtered, and the residue washed with water. The combined aqueous filtrates are concentrated in vacuo to the point of incipient precipitation, chilled and 150 ml of absolute alcohol added with rapid agitation to yield 4.37 g of 7-glycylaminocephalosporanic acid as the zwitterion.

This zwitterion salt, 3.29 g, is dissolved at room temperature in a mixture of 80 ml of water, 40 ml of acetone and 2.1 g of sodium bicarbonate. The mixture is cooled to 5° C. and 4.2 g of S-methyl-1,3-dithiolane-2-thione iodide, prepared in accordance with the procedure of Example 1 is added with stirring. The reaction mixture is permitted to warm to room temperature with stirring and concentrated to about 80 ml and extracted with diethylether. The aqueous layer is layered with ethyl acetate, acidified to pH 2.0 with a solution of 1 N hydrochloric acid, separated, and further extracted with additional ethyl acetate. The combined ethyl acetate extracts are combined, dried (MgSO4) and concentrated in vacuo to yield 0.88 g of the desired 7-[2-(1,3-dithiolan-2-imino)acetylamino]cephalosporanic acid. This compound is dissolved in 50 ml of chloroform, followed by the addition of 5-10 ml of methanol with good agitation and 1.5 ml of sodium 2-ethylhexanoate (2 M solution in butanol). The solution is filtered and 150 ml of ether is slowly added with good agitation to precipitate the sodium salt. The 7-[2-(1,3-dithiolan-2-imino)acetylamino]cephalosporanic acid, sodium salt is filtered, washed with ether and dried in vacuo to yield 0.92 g of material having a m.pt. of 138°-46° C. (dec.).

EXAMPLE 6

7-[2-(1,3-Dithiolan-2-imino)-2-phenylacetylamino]-desacetoxycephalosporanic acid, sodium salt The compound α-(1,3-dithiolan-2-imino)-α-phenylacetic acid, 2.53 g, and the t-butyl ester of 7-aminodesacetoxycephalosporanic acid are dissolved in 100 ml of chloroform and cooled to 5° C. and 2.47 g of the coupling agent 2-ethoxy-1-ethoxycarbonyl-1,2-dihydroquinoline added with stirring under an inert atmosphere of argon. The resulting solution is permitted to warm to room temperature and stirring continued for a period of about 16 hours. The reaction mixture is extracted twice with 50 ml portions of a 1 N hydrochloric acid solution, twice with 50 ml portions of a dilute sodium bicarbonate solution, dried (MgSO4) and evaporated in vacuo to dryness. The residue is crystallized from diethyl ether to yield 1.85 g of the t-butyl ester of 7-[2-(1,3-dithiolan-2-imino)-2-phenylacetylamino]-desacetoxycephalosporanic acid.

The t-butyl ester obtained in this manner, 1.01 g, is reacted with 5 ml of anhydrous trifluoroacetic acid at room temperature for a period of 15 minutes, poured into 100 ml of chloroform and evaporated in vacuo to dryness. The oily foam is triturated with diethyl ether to yield 1.12 g of an off-white solid. The free acid obtained in this manner is dissolved in 50 ml of methanol and 2.5 ml of sodium 2-ethylhexanoate (2 M solution in butanol). The reaction mixture is filtered and the desired salt is precipitated by the addition of 400 ml of anhydrous diethyl ether. The mixture is permitted to stand for one hour and filtered. The precipitate is washed twice with anhydrous ether and vacuum dried to yield 0.802 g of 7-[2-(1,3-dithiolan-2-imino)-2-phenylacetylamino]-desacetoxycephalosporanic acid as the sodium salt.

Following essentially the same procedure but substituting α-carboxy-α-(1,3-dithiolan-2-imino)acetic acid and α-(1,3-dithiolan-2-imino)-α-sulfoacetic acid for the α-(1,3-dithiolan-2-imino-α-phenylacetic acid above results in the preparation of 7-[2-carboxy-2-(1,3-dithiolan-2-imino)acetylamino]desacetoxycephalosporanic acid and 7-[2-(1,3-dithiolan-2-imino)-2-sulfoacetylamino]-desacetoxycephalosporanic acid as the sodium salts, respectively.

EXAMPLE 7

7-[2-[p-(1,3-dithiolan-2-imino)phenyl]acetylamino]-desacetoxycephalosporanic acid The compound 4-(1,3-dithiolan-2-imino)benzeneacetic acid (1.01 g), the t-butyl ester of 7-aminodesacetoxycephalosporanic acid (1.01 g) and the coupling agent 2-ethoxy-1-ethoxycarbonyl-1,2-dihydroquinoline (0.98 g) are mixed in 50 ml of chloroform containing 9 ml of sieve dried dimethylformamide. The reaction mixture is stirred under nitrogen gas for a period of approximately 20 hours. The reaction mixture is poured into a solution of 0.1 N hydrochloric acid solution, washed with three portions of a dilute aqueous sodium bicarbonate solution and washed with five separate portions of water. The organic layer is dried (MgSO4) and evaporated to dryness in vacuo.

The t-butyl ester of 7-[2-[p-(1,3-dithiolan-2-imino)-phenyl]acetylamino]desacetoxycephalosporanic so obtained is stirred with 10 ml of anhydrous trifluoroacetic acid at room temperature for a period of 15 minutes, diluted with approximately 50 ml of chloroform and evaporated to dryness in vacuo. Four successive portions of chloroform and one of benzene are added and the evaporation repeated. The dried residue is triturated with anhydrous ether to yield 1.85 g of the free acid as a yellow powder. The 7-[2-[p-(1,3-dithiolan-2-imino)-phenyl]acetylamino]desacetoxycephalosporanic acid is purified by dissolving in a small amount of acetone and pouring the resulting solution into 200 ml of anhydrous diethyl ether. The resulting light yellow powder is filtered, dried and has a m.pt. of 140°-50° C. (dec.).

Following essentially the same procedure but substituting 4-(1,3-dithiolan-2-imino)benzenethioacetic acid for the 4-(1,3-dithiolan-2-imino)benzeneacetic acid above results in the formation of 7-[2-[p-(1,3-dithiolan-2-imino)phenylthio]acetylamino]desacetoxycephalosporanic acid. Treatment of the free acid in a 3:2 chloroform-methanol solution with sodium 2-ethylhexanoate solution, followed by the addition of anhydrous ether results in the precipitation and isolation of 7-[2-[p-(1,3-dithiolan-2-imino)-phenylthio]acetylamino]desacetoxycephalosporanic acid as the sodium salt, having a m.pt. of 180°-90° C. (dec.).

Following essentially the same procedure as described for the title example, but substituting the t-butyl ester of 7-aminocephalosporanic acid for the 7-aminodesacetoxycephalosporanic acid results in the preparation of 7-[2-[p-(1,3-dithiolan-2-imino)phenyl]acetylamino]cephalosporanic acid. Treatment of the free acid with sodium 2-ethylhexanoate solution in methanol, followed by the addition of anhydrous ether results in the precipitation and isolation of 7-[2-[p-(1,3-dithiolan-2-imino)phenyl]acetylamino]cephalosporanic acid as the sodium salt, having a m.pt. of 150°-70° C. (dec.).

EXAMPLE 8

7-[2-Amino-2-[p-(1,3-dithiolan-2-imino)-phenyl]acetylamino]-3-[(5-methyl-1,3,4-thiadiazol-2-ylthio)-methyl]decephalosporanic acid The compound p-aminophenylglycine hydrochloride, 10.0 g, is dissolved in 100 ml of water, adjusted to its isoelectric point (pH approx. 4.8) by means of a 10% solution of sodium hydroxide, and 27.5 g of S-methyl 1,3-dithiolane-2-thione iodide is added in portions thereto. Following the addition of each portion of the dithiolane salt, the pH is readjusted to a pH of 4.8 using a 10% solution of sodium hydroxide. The reacting mixture is stirred overnight, adjusted to a pH of 12.0 using a 10% sodium hydroxide solution, extracted three times with ethyl acetate and once with diethyl ether. The aqueous layer is adjusted to a pH of 5.0 with concentrated hydrochloric acid. The white solid which forms is removed by filtration, washed with ethyl acetate and dried in vacuo to yield 6.40 g of α-amino-4-(1,3-dithiolan-2-imino)benzeneacetic acid having a m.pt. of 200°-5° C. The benzeneacetic acid so obtained, 4.2 g, is suspended in 25 ml of water containing 8.7 ml of triethylamine and stirred at room temperature until dissolved. A solution of 2.7 ml of t-butyloxycarbonylazide dissolved in 25 ml of p-dioxane is added and stirred for 18 hours at room temperature. The solution is concentrated to approximately ½ volume and extracted with diethyl ether. The aqueous layer is acidified with a 1 N solution of hydrochloric acid and extracted with ethyl acetate. The combined extracts are dried (MgSO4) and evaporated to dryness in vacuo to yield 3.3 g of the N-t-butyloxycarbonyl derivative of α-amino-4-(1,3-dithiolan-2-imino)benzeneacetic acid.

To a stirred mixture of 2.7 g of 7-aminocephalosporanic acid in 20 ml of water and 10 ml of acetone is added a saturated solution of sodium bicarbonate to a pH of 7.9. This solution is placed in an 80° C. bath and when the internal temperature reaches 45° C. a solution of 1.9 g of 2-methyl-1,3,4-thiadiazole-5-thiol in 20 ml of acetone is added. The mixture is heated in the 80° C. bath for three hours, cooled to 10° C. and the pH adjusted to 3.9 by the addition of 6 N hydrochloric acid. The cold mixture is stirred for 15 minutes, the solid is collected, washed with acetone, and dried. There is obtained 2.4 g of 7-amino-3-[(5-methyl-1,3,4-thiadiazol-2-ylthio)methyl]decephalosporanic acid.

A solution of 1.0 g of the N-t-butyloxycarbonyl derivative of α-amino-4-(1,3-dithiolan-2-imino)benzeneacetic acid, as prepared above, is dissolved in 20 ml of tetrahydrofuran containing 0.4 ml of triethylamine and cooled to −10° C. Isobutylchloroformate, 0.4 ml, is added and the mixture stirred at −10° C. for approximately 15 minutes. A chilled solution of 1.03 g of 7-amino-3-[(5-methyl-1,3,4-thiadiazol-2-ylthio)methyl]-decephalosporanic acid, as prepared above and dissolved in 30 ml of a 1:1 tetrahydrofuran-water solution containing 0.42 ml of triethylamine, is slowly added to the reaction mixture while maintaining the temperature at 0°-5° C. The reaction mixture is permitted to warm to room temperature, stirred for an additional 2-3 hours and poured into approximately 60 ml of water. The aqueous reaction mixture is extracted three times with 50 ml portions of ethyl acetate, layered with fresh ethyl acetate and the pH adjusted to 3.0 using a 1 N solution of hydrochloric acid. The ethyl acetate layer is separated and the aqueous layer extracted twice again with ethyl acetate. The combined organic extracts are dried (MgSO$_4$) and evaporated to dryness in vacuo to yield 0.7 g of the N-t-butyloxycarbonyl derivative of 7-[2-amino-2-[p-(1,3-dithiolan-2-imino)phenyl]acetylamino]-3-[(5-methyl-1,3,4-thiadiazol-2-ylthio)methyl]decephalosporanic acid. This material is treated at room temperature with 2 ml of trifluoroacetic acid for a period of 15 minutes and quenched by pouring into a stirred solution of 100 ml of anhydrous ethyl ether. The salt which precipitates is filtered, washed with anhydrous diethyl ether and dried to yield the trifluoroacetate salt of 7-[2-amino-2-[p-(1,3-dithiolan-2-imino)phenyl]acetylamino]-3-[(5-methyl-1,3,4-thiadiazol-2-ylthio)methyl]decephalosporanic acid. The trifluoroacetate salt is dissolved in methanol and adjusted to a pH of 5.0 with a 6 N solution of ammonium hydroxide. The solid which precipitates is collected, washed with acetone, ether and dried to yield 7-[2-amino-2-[p-(1,3-dithiolan-2-imino)phenyl]acetylamino]-3-[(5-methyl-1,3,4-thiadiazol-2-ylthio)methyl]decephalosporanic acid having a m.pt. of 165°-80° C. (dec.).

Following essentially the same procedure but substituting 1-methyl-1,2,3,4-tetrazole-5-thiol and 1,2,3-triazole-4-thiol for the 2-methyl-1,3,4-thiadiazole-5-thiol above results in the formation of 7-[2-amino-2-[p-(1,3-dithiolan-2-imino)phenyl]acetylamino]-3-[(1-methyl-1,2,3,4-tetrazol-5-ylthio)methyl]decephalosporanic acid and 7-[2-amino-2-[p-(1,3-dithiolan-2-imino)phenyl]acetylamino]-3-[(1,2,3-triazol-4-ylthio)methyl]decephalosporanic acid, respectively.

EXAMPLE 9

7-[2-Amino-2-[p-(1,3-dithiolan-2-imino)phenyl]acetylamino]desacetoxycephalosporanic acid To a solution of 2.0 g of the N-t-butyloxycarbonyl derivative of α-amino-4-(1,3-dithiolan-2-imino)benzeneacetic acid, prepared in accordance with the procedure of Example 8, in 100 ml of chloroform is added 1.47 g of the t-butyl ester of 7-aminodesacetoxycephalosporanic acid and 1.34 g of the coupling agent 2-ethoxy-1-ethoxycarbonyl-1,2-dihydroquinoline. The reaction mixture is stirred overnight at room temperature and quenched in a solution of 0.1 N hydrochloric acid. The reaction mixture is extracted an additional three times with a fresh 0.1 N hydrochloric acid solution, washed with three portions of a dilute sodium bicarbonate solution and washed with five separate portions of water. The chloroform layer is dried (MgSO$_4$) and evaporated to dryness in vacuo to yield 4.1 g of the N-t-butyloxycarbonyl derivative of t-butyl 7-[2-amino-2-[p-(1,3-dithiolan-2-imino)phenyl]acetylamino]desacetoxycephalosporanate. The protecting groups are removed by treating 3.37 g of this compound with 10 ml of trifluoroacetic acid for approximately 15 minutes at room temperature and pouring the reaction mixture into 300 ml of anhydrous diethyl ether. The trifluoroacetate salt which precipitates is converted to the free acid by dissolving 1.73 g of the salt in approximately 10 ml of methanol and carefully adjusting the pH of the resulting solution to a pH of 5.0 using a 6 N solution of ammonium hydroxide. The mixture is diluted with approximately 50 ml of acetone followed by approximately 200 ml of diethyl ether. The precipitate which forms is filtered, washed with diethyl ether to yield 1.30 g of the zwitterion of 7-[2-amino-2-[p-(1,3-dithiolan-2-imino)phenyl]acetylamino]desacetoxycephalosporanic acid, having a m.pt. of 185°-200° C. (dec.).

Following essentially the same procedure but substituting the t-butyl ester of 7-aminocephalosporanic acid for the 7-aminodesacetoxycephalosporanic acid above results in the preparation of 7-[2-amino-2-[p-(1,3-dithiolan-2-imino)phenyl]acetylamino]cephalosporanic acid having a m.pt. of 150°-70° C. (dec.).

EXAMPLE 10

7-[2-[p-(1,3-Dithiolan-2-imino)phenyl]-2-hydroxyacetylamino]cephalosporanic acid, sodium salt The compound p-aminomandelic acid, 1.67 g, and 20 ml of triethylamine are dissolved in 20 ml of sieve-dried dimethylformamide and 3.06 g of S-methyl 1,3-dithiolane-2-thione iodide added thereto. The reaction mixture is stirred at room temperature for a period of 2 hours and quenched in 60 ml of an ice cold sodium bicarbonate solution. The resulting mixture is extracted three times with 50 ml portions of methylene chloride and once more with 50 ml of diethyl ether. The aqueous layer is acidified to a pH of 1.0 using concentrated hydrochloric acid, whereupon a white solid precipitates. The precipitate is removed by filtration, washed twice with water, followed by a cold ethanol and ether wash, and air dried to yield 1.46 g of 4-(1,3-dithiolan-2-imino)-α-hydroxy-benzeneacetic acid having a m.pt. of 184°-7° C.

The α-hydroxy acid prepared in this manner is dissolved in 25 ml of tetrahydrofuran containing 0.83 ml of triethylamine and 0.8 ml of bistrimethylsilylacetamide, which is commercially available, added thereto. The reaction mixture is refluxed for a period of 1.5 hours, cooled to −10° C. and 0.8 ml of isobutylchloroformate contained in 1 ml of tetrahydrofuran added in dropwise fashion thereto. The compound 7-aminocephalosporanic acid, 1.63 g, is dissolved in a solution of 12 ml of water, 12 ml of tetrahydrofuran and 1.0 ml of triethylamine, filtered and added to the protected α-hydroxy acid mixed anhydride solution while maintaining the temperature at −5° to −10° C. The reaction mixture is stirred at −5° C. for one hour and permitted to warm to room temperature with continued stirring for an additional 1.5 hours. The reaction mixture is poured into 150 ml of water, evaporated to ½ volume in vacuo and extracted with three portions each of ethylacetate. The aqueous solution is layered with ethyl acetate and the pH adjusted to 1.5 using a concentrated hydrochloric acid solution. The unreacted 7-aminocephalosporanic acid which precipitates is removed by filtration. The aqueous solution is extracted twice again with ethyl acetate, the ethyl acetate extracts are combined, dried (MgSO₄), filtered and evaporated to dryness in vacuo. The residue is triturated with anhydrous diethyl ether, filtered and dried to yield 2.1 g of 7-[2-[p-(1,3-dithiolan-2-imino)phenyl]-2-hydroxyacetylamino]cephalosporanic acid. The free acid, 1.35 g, is dissolved in 30 ml of a 1:1 methanolisopropyl alcohol solution, filtered and treated with 2.6 ml of a sodium-2-ethylhexanoate solution (2 M in butanol). Diethyl ether is added and the sodium salt which precipitates is removed by filtration, washed twice with cold isopropyl alcohol, followed by two diethyl ether washes and dried in vacuo to yield 0.87 g of 7-[2-[p-(1,3-dithiolan-2-imino)phenyl]-2-hydroxyacetylamino]cephalosporanic acid, sodium salt having a m.pt. of 150°–80° C. (dec.).

Following essentially the same procedure but substituting 7-aminodesacetylcephalosporanic acid and 7-aminodesacetoxycephalosporanic acid for the 7-aminocephalosporanic acid above results in the formation of 7-[2-[p-(1,3-dithiolan-2-imino)phenyl]-2-hydroxyacetylamino]-desacetylcephalosporanic acid, sodium salt and 7-[2-[p-(1,3-dithiolan-2-imino)phenyl]-2-hydroxyacetylamino]-desacetoxycephalosporanic acid, sodium salt, respectively.

EXAMPLE 11

The following example illustrates the in vitro activity of the compounds of this invention.

Two-fold serial dilutions of the test compounds are made in trypticase soy broth. A series of tubes of broth containing different concentrations of the test compounds are inoculated with the particular bacterial culture used for in vitro activity. The inoculated tubes are examined for the inhibition of bacterial growth after 24 hours of incubation at 37° C. The following table summarizes the minimal inhibitory concentration (MIC) for various bacterial test cultures using the following compounds:

Compound A = 7-[2-(1,3-dithiolan-2-imino)acetylamino]cephalosporanic acid
Compound B = 7-[2-(1,3-dithiolan-2-imino)-2-phenylacetylamino]desacetoxycephalosporanic acid
Compound C = 7-[2-amino-2-[p-(1,3-dithiolan-2-imino)-phenyl]acetylamino]desacetoxycephalosporanic acid
Compound D = 7-[2-[p-(1,3-dithiolan-2-imino)phenyl]-2-hydroxyacetylamino]cephalosporanic acid

| Organism | MIC (mcg/ml) for Compounds | | | |
|---|---|---|---|---|
| | A | B | C | D |
| Staphylococcus aureus | 0.4 | 25 | 3.1 | 0.4 |
| Streptococcus pyogenes | 0.4 | 6.2 | ≦0.05 | <0.05 |
| Diplococcus pneumonae | 0.1 | 12.5 | ≦0.05 | <0.05 |
| Salmonella schottmuelleri | 12.5 | >100 | >100 | 50 |
| Escherichia coli | 50 | >100 | >100 | 200 |

EXAMPLE 12

The following example illustrates the in vivo activity of the compounds of this invention.

Several groups of 10 mice are challenged with a fatal bacterial infection. Various dose levels of the test compound are administered orally or subcutaneously to separate groups of these animals 1 and 4 hours after challenge. After three of four days, depending upon the test organism, the number of survivors are recorded at each dose level and the dose required per treatment to protect fifty percent of the infected mice (ED₅₀) is calculated by the method described by Reed and Muench, Amer. J. Hyg. 27, 493–497 (1938).

Compounds are as indicated in Example 11 above.

| Organism | ED₅₀ (mg/Kg/dose) for Compounds | | | |
|---|---|---|---|---|
| | A | B | C | D |
| Streptococcus pyogenes | 15.3(sc) | 48(sc) | 0.5(sc) | 2.2(sc) |
| Diplococcus pneumoniae | — | — | 5(sc) 4.1(po) | — |
| Salmonella schotmuelleri | — | — | >100(sc) | — | sc = subcutaneous
po = per os

We claim:
1. A 7-[2-[ω-(1,3-dithiolan-2-imino)substituted-]acetylamino]cephalosporanic acid derivative having the formula

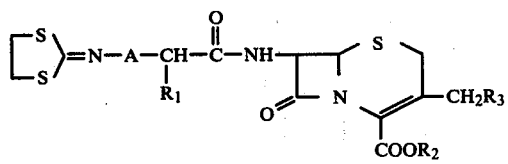

wherein
A is selected from the group consisting of a sigma bond, phenylene and phenylenethio;
R₁ is selected from the group consisting of hydrogen, phenyl, amino, hydroxy, carboxy and sulfo;
R₂ is selected from the group consisting of hydrogen formyloxymethyl and alkanoyloxymethyl in which the alkanoyl group contains from 2 to 5 carbon atoms;
R₃ is selected from the group consisting of hydrogen, hydroxy, acetoxy, 5-methyl-1,3,4-thiadiazol-2-ylthio, 1-methyl-1,2,3,4-tetrazol-5-ylthio and 1,2,3-triazol-4-ylthio; and the pharmaceutically acceptable salts thereof.

2. A compound according to claim 1 wherein A is a sigma bond.

3. A compound according to claim 1 wherein A is a phenylene group.

4. A compound according to claim 1 wherein $R_3$ is hydrogen or acetoxy.

5. A compound according to claim 1 which is 7-[2-(1,3-dithiolan-2-imino)acetylamino]cephalosporanic acid.

6. A compound according to claim 1 which is 7-[2-[p-(1,3-dithiolan-2-imino)phenyl]-2-hydroxyacetylamino]-cephalosporanic acid.

7. A compound according to claim 1 which is 7-[2-(1,3-dithiolan-2-imino)-2-phenylacetylamino]desacetoxycephalosporanic acid.

8. A compound according to claim 1 which is 7-[2-amino-2-[p-(1,3-dithiolan-2-imino)phenyl]acetylamino]-desacetoxycephalosporanic acid.

* * * * *